United States Patent
Venkatesh et al.

(10) Patent No.: US 11,085,915 B2
(45) Date of Patent: Aug. 10, 2021

(54) METHOD, CONTROL UNIT, AND DEVICE FOR DETECTING A GASEOUS SUBSTANCE IN A GAS MIXTURE

(71) Applicant: Robert Bosch GmBH, Stuttgart (DE)

(72) Inventors: Rajeev H. Venkatesh, Arehalli (IN); Mary Thomas, Koramangala (IN); Ye Lu, Reutlingen (DE)

(73) Assignee: Robert Bosch GmBH, Stuttgart (DE)

( * ) Notice: Subject to any disclaimer, the term of this patent is extended or adjusted under 35 U.S.C. 154(b) by 125 days.

(21) Appl. No.: 16/607,841

(22) PCT Filed: Apr. 20, 2018

(86) PCT No.: PCT/EP2018/060131
§ 371 (c)(1),
(2) Date: Oct. 24, 2019

(87) PCT Pub. No.: WO2018/197345
PCT Pub. Date: Nov. 1, 2018

(65) Prior Publication Data
US 2020/0132669 A1    Apr. 30, 2020

(30) Foreign Application Priority Data

Apr. 25, 2017 (DE) ...................... 10 2017 206 878.7

(51) Int. Cl.
*G01N 33/497* (2006.01)
*G01N 33/00* (2006.01)

(52) U.S. Cl.
CPC ..... *G01N 33/4972* (2013.01); *G01N 33/0016* (2013.01)

(58) Field of Classification Search
CPC .. G01N 33/00; G01N 33/0016; G01N 33/497; G01N 33/4972; A61B 5/08–083; A61B 5/097
See application file for complete search history.

(56) References Cited

U.S. PATENT DOCUMENTS 4,749,553 A * 6/1988 Lopez ................ G01N 33/4972
180/272
5,303,575 A * 4/1994 Brown ............... G01N 33/4972
422/84
(Continued)

FOREIGN PATENT DOCUMENTS

DE    2610578 A1    9/1977
DE    2746078 A1    4/1979
(Continued)

OTHER PUBLICATIONS

International Search Report for PCT/EP2018/060131, dated Jul. 18, 2018.

*Primary Examiner* — Nguyen Q. Ha
(74) *Attorney, Agent, or Firm* — Norton Rose Fulbright US LLP; Gerard Messina

(57) ABSTRACT

A method for detecting a gaseous substance in a gas-mixture, a first measuring-variable which represents a first chemical and/or physical parameter of the gas-mixture being acquired, at least one second measuring-variable which represents a second chemical and/or physical parameter of the gas-mixture that differs from the first parameter being acquired, and a starting-measuring-instant, corresponding to the starting-instant, of the first parameter is specified when an amount of a time-derivative of the first measuring-variable exceeds a first predefined threshold-value and an amount of a time-derivative of the second measuring-variable exceeds a second predefined threshold-value, and at least one further first measuring-variable is acquired, an end instant is specified when the at least one further first measuring-variable corresponds to the starting measuring-variable, and an output signal is generated when the amount of a difference between the end instant and the starting instant is greater than a predefined minimum time span.

10 Claims, 5 Drawing Sheets

(56) References Cited

U.S. PATENT DOCUMENTS

| | | | | |
|---|---|---|---|---|
| 5,971,937 | A | * 10/1999 | Ekstrom | G01N 33/4972 |
| | | | | 422/84 |
| 2004/0081582 | A1 | 4/2004 | Brook | |
| 2004/0138823 | A1* | 7/2004 | Gollar | B60K 28/063 |
| | | | | 702/19 |
| 2008/0214948 | A1 | 9/2008 | Myklebust et al. | |
| 2014/0165698 | A1* | 6/2014 | Mochizuki | G01N 33/4972 |
| | | | | 73/23.3 |
| 2001/4357963 | | 12/2014 | Chang | |
| 2014/0377877 | A1* | 12/2014 | Burgi | G01N 33/4972 |
| | | | | 436/120 |

FOREIGN PATENT DOCUMENTS

| | | |
|---|---|---|
| DE | 102015203719 A1 | 9/2016 |
| EP | 2878949 A1 | 6/2015 |
| EP | 2891883 A1 | 7/2015 |
| EP | 3144669 A1 | 3/2017 |
| JP | 2004125433 A | 4/2004 |
| JP | 2010518375 A | 5/2010 |
| JP | 2011232058 A | 11/2011 |

\* cited by examiner

METHOD, CONTROL UNIT, AND DEVICE FOR DETECTING A GASEOUS SUBSTANCE IN A GAS MIXTURE

FIELD OF THE INVENTION

The present invention is based on a method, a control unit, and a device.

BACKGROUND INFORMATION

Breath gas analysis devices can analyze a composition and especially also a smell of breath gas via chemical or physical sensors. Among other things, an alcohol content in the breath gas is also of interest.

From the document US 2004/0081582 A1, a mobile telephone is discussed, which is equipped with a breath gas sensor so that a user of the mobile telephone can have the quality of his or her breath displayed.

The document US 2014/0357963 A1 discusses a portable electronic device which has an optical sensor by which an alcohol concentration of a breath gas can be detected.

From the document DE 10 2015 203 719 A1, a device for a breath gas analysis is discussed, which has a sensor element for detecting at least one analyte in a breath gas condensate volume.

SUMMARY OF THE INVENTION

Against this background, the presented approach introduces a method for detecting a gaseous substance, in particular ethanol, in a gas mixture with the aid of a gas sensor; a control unit for carrying out the method, and also a gas sensor. The gas sensor may be developed as a mobile, handheld device which a user may employ in order to determine an alcohol concentration or an ethanol concentration of his or her breath. For this purpose, the gas sensor may advantageously have an orifice into which the user may blow or breathe.

In the present method, at least one first measuring variable is initially acquired using a first sensor element and at least one second measuring variable is acquired using a second sensor element. The first measuring variable represents a first chemical and/or physical parameter of the gas mixture, in particular an ethanol concentration. The first sensor element may be developed as a gas sensor, in particular as a resistive, capacitive, potentiometric and/or amperometric gas sensor. The second measuring variable represents a second chemical and/or physical parameter of the gas mixture which differs from the first chemical and/or physical parameter, in particular a temperature, a humidity or a pressure. The second sensor element may be developed as a temperature sensor, a humidity sensor and/or as a pressure sensor. Alternatively or additionally, it is possible that the first and/or the second sensor element is/are developed to acquire at least two different measuring variables, the two different measuring variables representing two different chemical and/or physical parameters of the gas mixture in each case.

In order to determine a starting instant of a measurement, a second time derivative of the acquired first measuring variables may be formed and compared to a first predefined threshold value. By forming a time derivative of the acquired second measuring variables and a comparison with a second predefined threshold value, an accuracy with which the starting instant of the measurement is determined is advantageously able to be increased. As a whole, this makes the measurement more reliable and robust with respect to external influencing factors such as changes in a composition of the gas mixture.

Simultaneously with the determination and storing of the starting instant, a first measuring variable, acquired at the starting instant, is stored. Further first measuring variables are subsequently acquired, which may be on a continuous basis. The measurement is terminated when one of the additionally acquired first measuring variables essentially corresponds to the first measuring variable stored at the starting instant, in that an end instant that corresponds to the further first measuring variable is stored.

Next, a difference is formed between the end instant and the starting instant, and an amount of this difference is compared to a predefined minimum time span. In this case, the difference corresponds to a quantitative indication of the chemical and/or physical parameter of the gas mixture represented by the first measuring variable. If the difference corresponds to the predefined minimum time span or if the difference exceeds the predefined minimum time span, then an output signal is generated, which signals that the first measuring variable representing the first chemical and/or physical parameter of the gas mixture lies above a predefined threshold value.

If a third measuring variable or additionally also a fourth measuring variable is/are then optionally acquired as well, the third measuring variable and the fourth measuring variable representing a further chemical and/or physical parameter of the gas mixture in each case, especially a temperature, a humidity or a pressure, the parameters represented by the first measuring variable, the second measuring variable, the third measuring variable and the fourth measuring variable differing, and if for each additionally acquired measuring variable a time derivative is formed and compared to a further predefined threshold value in each case, then the accuracy with which the starting instant of the measurement is determined is able to be increased even further.

It may optionally be the case that the measurement is terminated when a relative deviation of the amount between the at least one further first measuring variable and the first measuring variable acquired at the starting instant is smaller than a predefined threshold value, which may be smaller than 5%, especially particularly smaller than 1%, and most particularly smaller than 0.1%.

The previously mentioned advantages similarly apply also to the control unit for carrying out the present method and to the gas sensor.

Additional advantages result from the following description of the exemplary embodiments.

DETAILED DESCRIPTION

As already described earlier, the present invention describes a method, a control unit and a device by which an accuracy in a determination of a starting instant during a measurement of at least one gaseous substance in a gas mixture, in particular ethanol, is increased and the accuracy of the measurement is therefore greater as a whole.

Figure 1:
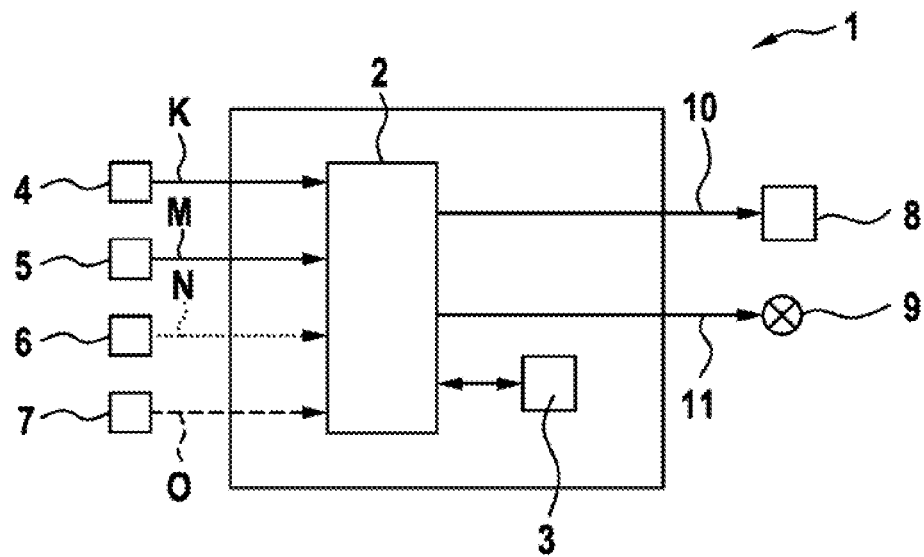
FIG. 1 schematically shows a block diagram of a control unit.

A control unit 1 as schematically illustrated in FIG. 1 is provided for executing the present method. This control unit 1 acquires a first measuring variable K, which represents an ethanol concentration of a breath gas, with the aid of a first sensor element 4, and a second measuring variable M, which represents a further physical and/or chemical parameter of the breath gas such as a temperature, with the aid of a second sensor element 5.

It may optionally be provided that control unit 1 additionally acquires a third measuring variable N, which represents a further physical and/or chemical parameter of the breath gas such as a humidity, with the aid of a third sensor element 6, and/or a fourth measuring variable O, which represents a further physical and/or chemical parameter of the breath gas such as a pressure, with the aid of a fourth sensor element 7.

If required, the acquired measuring variables K, M, N and O are able to be stored in memory unit 3 of device 1.

First sensor element 4 may be developed as a gas sensor, in particular as a resistive, capacitive, potentiometric and/or amperometric gas sensor. Second sensor element 5 may be developed as a temperature sensor. Third sensor element 6 may be developed as a humidity sensor. Fourth sensor element 7 may be developed as a pressure sensor. Alternatively or additionally, it is possible that one of sensor elements 4, 5, 6, 7 is developed to acquire at least two different measuring variables, the two different measuring variables representing two different chemical and/or physical parameters of the gas mixture in each case.

Figure 2:
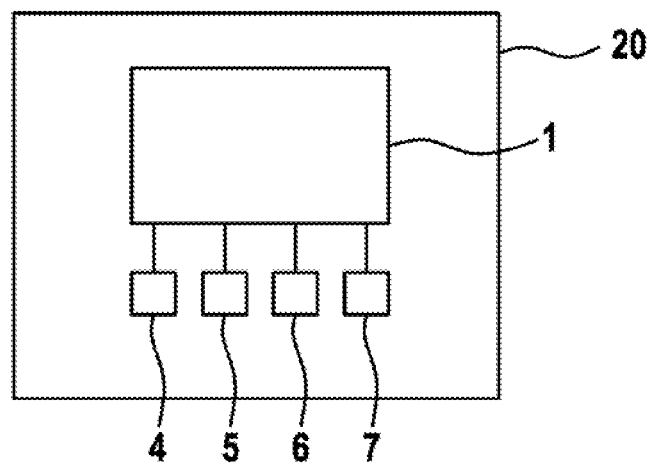
FIG. 2 shows a schematic illustration of a gas sensor.

Control unit 1 and first sensor element 4 as well as second sensor element 5 may form a gas sensor 20, as schematically illustrated in FIG. 2. It may optionally be provided that the gas sensor additionally includes a third sensor element 6 and/or a fourth sensor element 7. Moreover, it may be provided that sensor elements 4, 5, 6, 7 are situated on the gas sensor or are integrated into the gas sensor.

On the basis of the acquired measuring variables K and M as well as the optionally acquired measuring variables N and O, an arithmetic unit 2 in control unit 1 carries out method 100 described in the following text and generates an output signal 10 as a function of acquired measuring variables K, M, N and O, the output signal actuating an acoustic signal transducer 8, for example. A further output signal 11 may optionally be generated, which actuates an optical signal transducer 9. Acoustic signal transducer 8 may be developed as a loudspeaker. Optical signal transducer 9 may be developed as a light-emitting diode and/or as a display.

Figure 3:
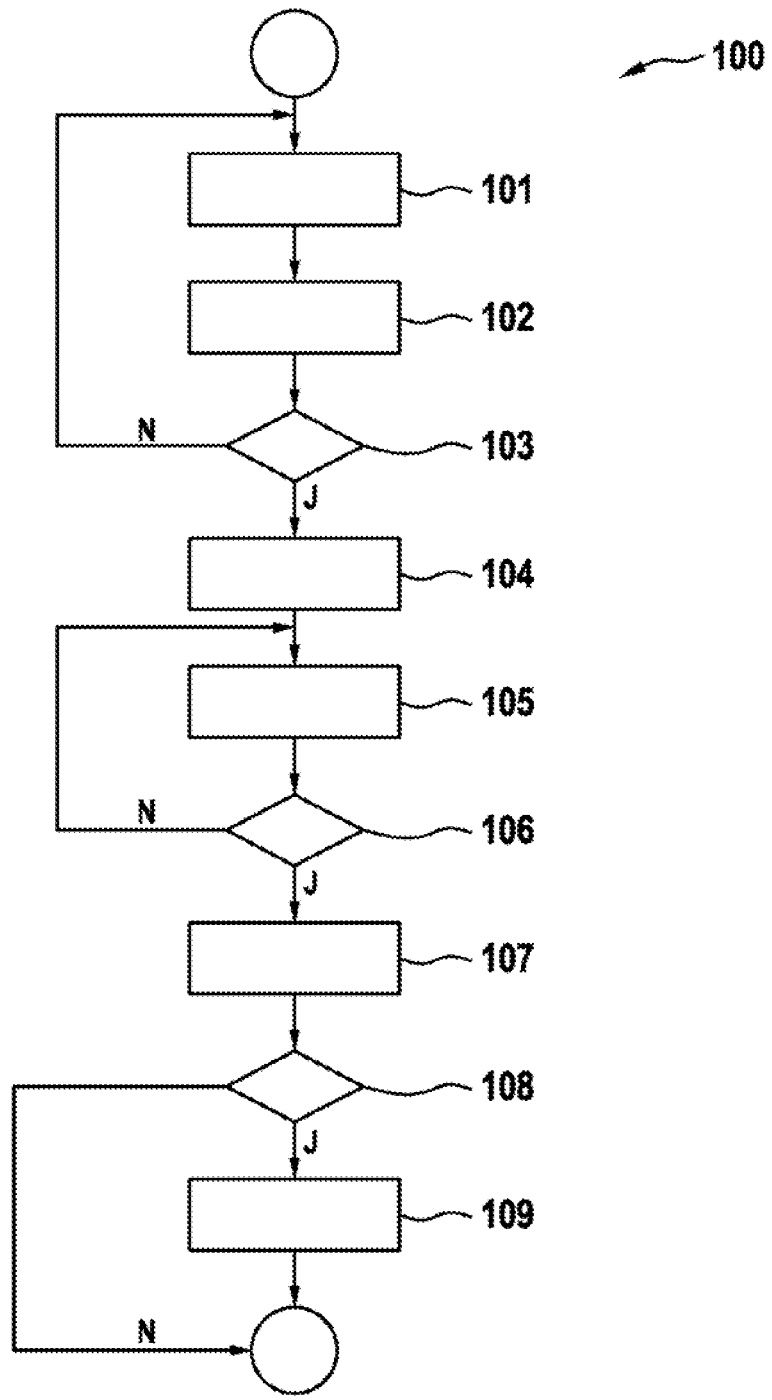
FIG. 3 shows the present method with the aid of a flow diagram.

Based on the flow diagram of FIG. 3, method 100 is described in an exemplary embodiment. To begin with, first measuring variable K, which represents an ethanol concentration in a breath gas, is acquired in a first acquisition step 101.

A second acquisition step 102 takes place prior to, during or following acquisition step 101, in which a temperature of the breath gas is acquired as a second measuring variable M.

A humidity of the breath gas may optionally be acquired as a third measuring variable N and/or a pressure as a fourth measuring variable O in acquisition step 101.

Next, an amount of the time derivative of acquired first measuring variable K is compared to threshold value $SW_1$ in a subsequent first method step 103, and an amount of the time derivative of the acquired second measuring variable M is compared to threshold value $SW_2$.

Optionally, the amount of the time derivative of acquired third measuring variable N is additionally compared to threshold value $SW_3$ in comparison step 103. The amount of the time derivative of acquired fourth measuring variable O is optionally compared to threshold value $SW_4$ in comparison step 103.

If the amount of the time derivative of first measuring variable K lies above first threshold value $SW_1$, and if the amount of the time derivative of second measuring variable M lies above second threshold value $SW_2$, then a starting instant $t_s$ and a starting measuring variable $K_{start}$ corresponding to starting instant $t_s$ are specified in a first specification step 104.

It may optionally be provided that the first specification step 104 is carried out only when the amount of the time derivative of third measuring variable N is additionally above third threshold value $SW_3$ and/or if the amount of the time derivative of fourth measuring variable O lies above fourth threshold value $SW_4$.

If the amount of the time derivative of first measuring variable K does not lie above first threshold value $SW_1$ or if the amount of the time derivative of second measuring variable M does not lie above second threshold value $SW_2$, then the first acquisition step 101 will be carried out again.

Optionally, first acquisition step 101 may take place if, alternatively or additionally, the amount of the time derivative of third measuring variable N does not lie above third threshold value $SW_3$ or if the amount of the time derivative of fourth measuring variable O does not lie above fourth threshold value $SW_4$.

First specification step 104 is followed by a third acquisition step 105 during which at least one further first measuring variable $K_2$ is acquired, and in a second comparison step 106, a comparison takes place in order to determine whether the at least one further first measuring variable $K_2$ essentially corresponds to starting measuring variable $K_{start}$. If this is the case, then an end instant $t_E$ is specified in a following, second specification step 107. End instant $t_E$ may then optionally be specified when a relative deviation of the amount between the at least one further first measuring variable $K_2$ and starting measuring variable $K_{Start}$ is smaller than a fifth predefined threshold value $SW_5$, in particular smaller than 5%. In an alternative development of the present invention, it may be provided that end instant $t_E$ is specified to follow a predefined time span after starting instant $t_S$. If the comparison in second comparison step 106 is negative, then third acquisition step 105 is carried out again.

After second specification step 107, a third comparison step 108 takes place in which it is compared whether the amount of a difference between end instant $t_E$ and starting instant $t_S$ is greater than a predefined minimum time span $t_{min}$. Alternatively or additionally, it may be provided that a comparison takes place in third comparison step 108 in order to determine whether the amount of an already elapsed time period since starting instant $t_S$ is greater than a predefined minimum time span $t_{min}$. In addition, it may alternatively or additionally be provided that during third comparison step 108, a comparison takes place after a predefined minimum time span $t_{min}$ to determine whether the at least one further first measuring variable $K_2$ is smaller than starting measuring variable $K_{Start}$. If this is not the case, the measurement will be terminated and a new measurement may optionally be carried out. If comparison step 108 is positive, however, then an output signal 10, which is able to be converted into a signal tone with the aid of a loudspeaker, for instance, is generated in a subsequent signal-generation step 109. It may optionally be provided that a further output signal 11 is generated, which is converted into an optical signal with the aid of an LED, for example. This acoustic or optical signal indicates to a user of gas sensor 20 that the ethanol concentration in the breath gas mixture, i.e. in his or her breath, lies above a previously specified value.

Figure 4:
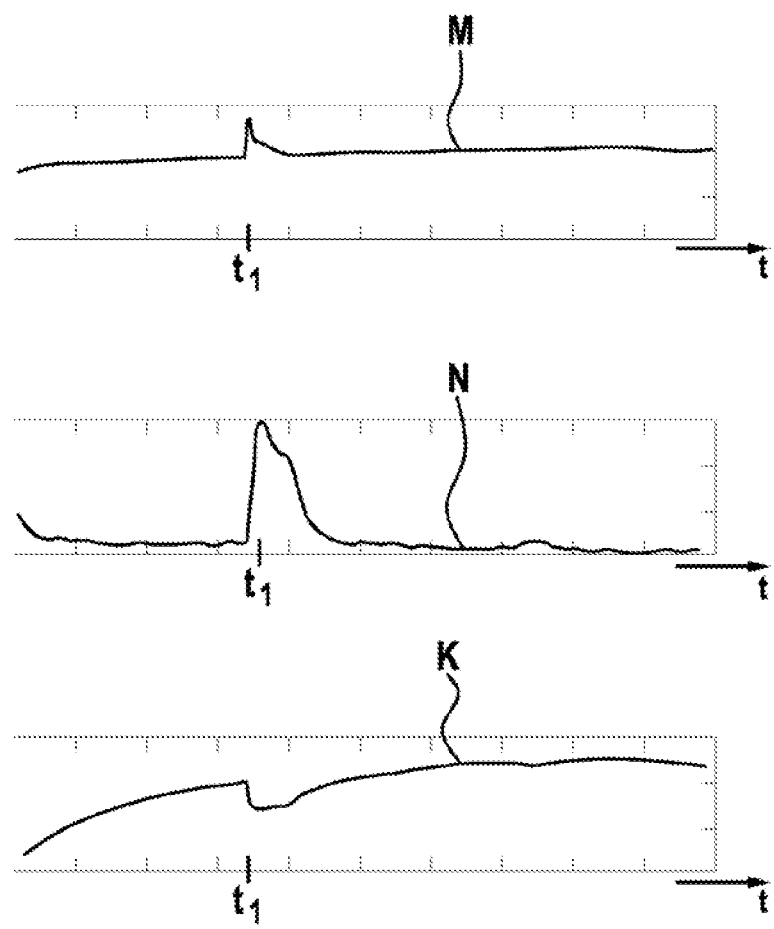
FIG. 4 shows a graphical illustration of a time characteristic of measuring variables representing a temperature, a humidity and an ethanol concentration of a gas mixture.

FIG. 4 shows graphical illustrations of a time characteristic of different measuring variables. The upper illustration represents time characteristic t of measuring variable M representing a temperature of the breath gas. The center illustration represents time characteristic t of a measuring variable N representing a humidity of the breath gas. The lower illustration shows time characteristic t of measuring variable K representing an ethanol concentration of the breath gas.

At an instant $t_1$, an essentially simultaneous change in the time characteristic of measuring variables M, N and K can be noticed. This change is caused by a user breathing into the gas sensor. In order to then determine the precise starting instant $t_{Start}$ of the change in the time characteristics of measuring variables M, N and K, or in other words, to determine a measuring start, time derivatives $\dot{M}$, $\dot{N}$ and $\dot{K}$ of acquired measuring variables M, N and K are formed.

Figure 5:
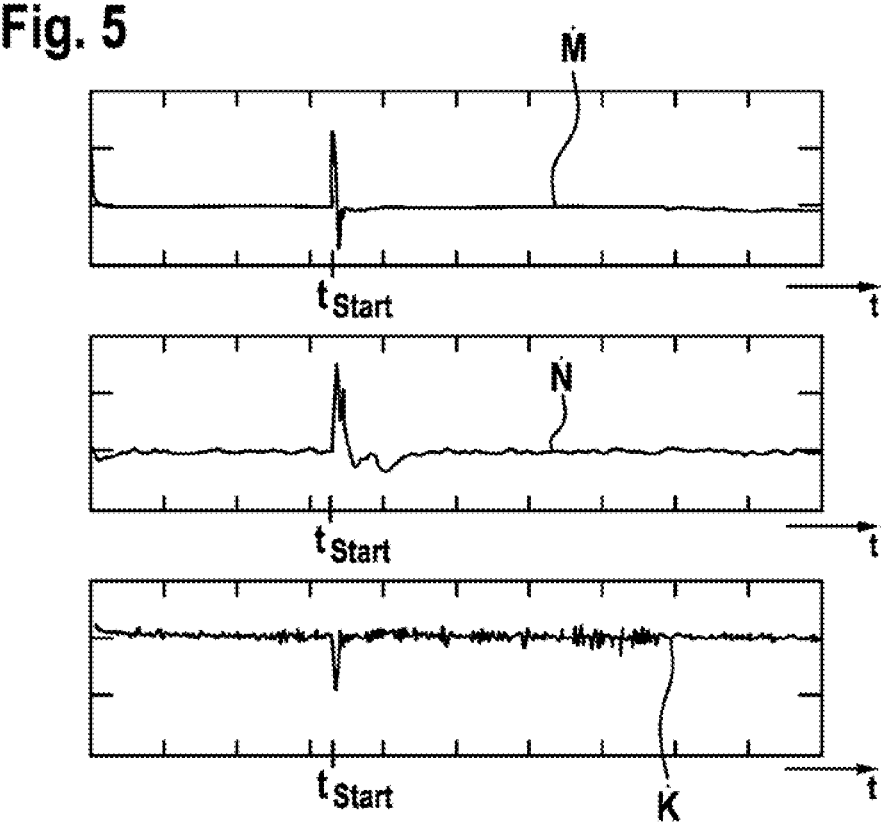
FIG. 5 shows graphical representations of a time characteristic of time derivatives of the measuring variables shown in FIG. 3.

These time derivatives $\dot{M}$, $\dot{N}$ and $\dot{K}$ of acquired measuring variables M, N and K are graphically illustrated in FIG. 5. It can be seen quite clearly that the change in the time characteristics occurs virtually simultaneously in all three time derivatives $\dot{M}$, $\dot{N}$ and $\dot{K}$ of acquired measuring variables M, N and K. The determination of starting instant $t_{Start}$ of the measurement is therefore able to be significantly improved in that additional measuring variables which represent further chemical and/or physical parameters of the breath gas are taken into account.

Figure 6:
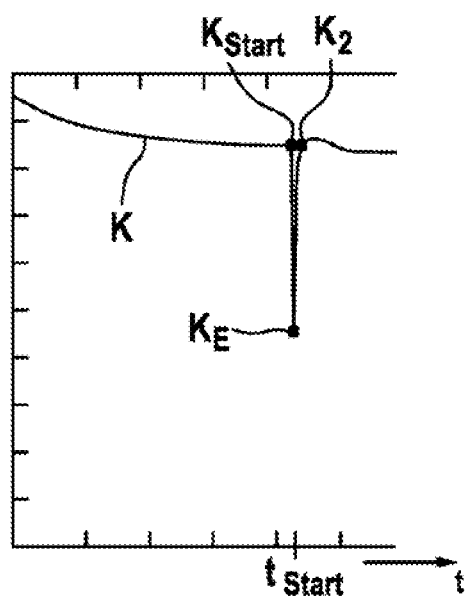
FIG. 6 shows a graphical representation of a measurement of an ethanol concentration in a breath gas over the time without any previous alcohol consumption of a user.

FIG. 6 shows an additional graphical illustration of a time characteristic of a measurement of measuring variable K, which represents an ethanol concentration in a breath gas without any previous alcohol consumption of a user. As described with the aid of FIG. 5, starting instant $T_{Start}$ is accurately able to be determined by forming the time derivative $\dot{K}$ of measuring variable K and at least one further time derivative of, for instance, measuring variable M, which represents the temperature of the breath gas. A measuring variable K acquired at this starting instant $t_{Start}$ is stored as a corresponding starting measuring variable $K_{Start}$ in memory unit 3. It can be seen that measuring variable K drops to a minimum $K_E$ and then rises again. Here, minimum $K_E$ merely represents a value of measuring variable K at an instant when the user is no longer breathing into the gas sensor and at which the ethanol concentration in sensor element 4 sensing the ethanol concentration in the breath gas mixture begins to regenerate. Sensor element 4 is completely regenerated when a further first measuring variable $K_2$ essentially corresponds to starting measuring variable $K_{Start}$. An end instant $t_E$ corresponding to further first measuring variable $K_2$ is specified and stored in memory unit 3. The time difference between $t_E$ and $t_{Start}$ is a measure of the ethanol concentration in the breath gas of the user.

Figure 7:
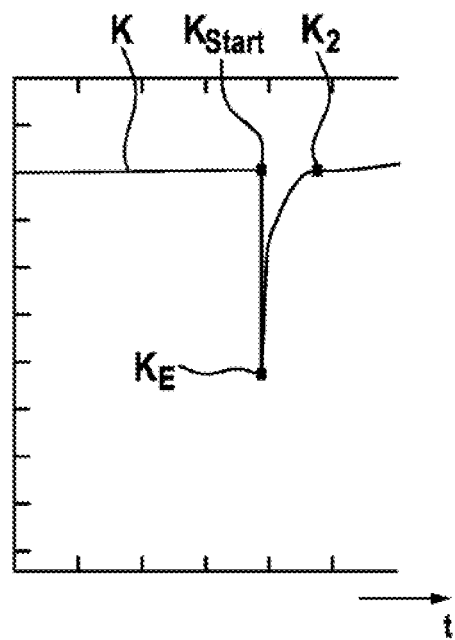
FIG. 7 graphically illustrates a measurement of an ethanol concentration in a breath gas over the time with a previous alcohol consumption of the user.

For comparison purposes, a further graphical illustration of the time characteristic of a measurement of measuring variable K which represents an ethanol concentration in a breath gas with a previous alcohol consumption of a user is shown in FIG. 7 at the same scale. It can be seen quite clearly that the time difference between $t_E$ and $t_{Start}$ is greater than in the measurement without any previous alcohol consumption by the user from FIG. 6. It may be provided as a function of a certain predefined minimum time span $t_{min}$ previously stored in memory unit 3 that gas sensor 20 outputs a signal 10, 11 to the user in order to draw his or her attention to the fact that the ethanol concentration in the user's breath exceeds a threshold value represented by minimum time span $t_{min}$.

What is claimed is:

1. A method for detecting a gaseous substance and/or ethanol, in a gas mixture with the aid of a gas sensor, the method comprising:
   performing the following:
   a first acquisition, in which at least one first measuring variable which represents a first chemical and/or physical parameter of the gas mixture, in particular a concentration of ethanol, is acquired using a first sensor element;
   a second acquisition, in which at least one second measuring variable which represents a second chemical and/or physical parameter of the gas mixture that differs from the first chemical and/or physical parameter, in particular a temperature, a pressure or a humidity, is acquired using a second sensor element,
   a first comparison, in which a comparison takes place as to whether an amount of a time derivative of the first measuring variable exceeds a first predefined threshold value and whether an amount of a time derivative of the second measuring variable exceeds a second predefined threshold value,
   a first specification, in which a starting instant and a starting measuring variable, corresponding to the starting instant, of the first chemical and/or physical parameter is specified when the first comparison is positive,
   a third acquisition, in which at least one further first measuring variable is acquired,
   a second comparison, in which a comparison takes place as to whether the at least one further first measuring variable corresponds to the starting measuring variable;
   a second specification, in which an end instant is specified when the second comparison is positive;
   a third comparison, in which a comparison takes place as to whether the amount of a difference between the end instant and the starting instant is greater than a predefined minimum time span, and
   a signal-generation, in which an output signal is generated when the third comparison is positive.

2. The method of claim 1, wherein in the second acquisition, at least one third measuring variable which represents a chemical and/or physical parameter of the gas mixture that differs from the first and second chemical and/or physical parameter(s) is additionally acquired using a third sensor element, and wherein in the first comparison, an additional comparison takes place as to whether an amount of a time derivative of the third measuring variable exceeds a third predefined threshold value.

3. The method of claim 2, wherein in the second acquisition, at least one fourth measuring variable which represents a chemical and/or physical parameter of the gas mixture which differs from the first, second and third chemical and/or physical parameter(s) is additionally acquired using a fourth sensor element, and wherein in the first comparison, an additional comparison takes place as to whether an amount of a time derivative of the fourth measuring variable exceeds a fourth predefined threshold value.

4. The method of claim 1, wherein the second comparison is positive when a relative deviation of the amount between the at least one further first measuring variable and the starting measuring variable is smaller than a fifth predefined threshold value, in particular smaller than 5%.

5. A control unit for detecting a gaseous substance and/or ethanol, in a gas mixture with the aid of a gas sensor, comprising:
   a memory unit; and
   an arithmetic unit configured to perform the following:
      in a first acquisition, to acquire at least one first measuring variable which represents a first chemical and/or physical parameter of the gas mixture, in particular a concentration of ethanol, using a first sensor element, and
      in a second acquisition, to acquire at least one second measuring variable which represents a second chemical and/or physical parameter of the gas mixture that differs from the first chemical and/or physical parameter, in particular a temperature, a pressure or a humidity, using a second sensor element,
      in a first comparison, to carry out a comparison as to whether an amount of a time derivative of the first measuring variable exceeds a first predefined threshold value and whether an amount of a time derivative of the second measuring variable exceeds a second predefined threshold value,
      in a first specification, to specify a starting instant and a starting measuring variable, corresponding to the starting instant, of the first chemical and/or physical parameter when the first comparison is positive,
      in a third acquisition, to detect at least one further first measuring variable,
      in a second comparison, to compare whether the at least one further first measuring variable corresponds to the starting measuring variable,
      in a second specification, to specify an end instant when the second comparison is positive,
      in a third comparison, to compare whether the amount of a difference between the end instant and the starting instant is greater than a predefined minimum time span, and
      in a signal-generation, to generate an output signal when the third comparison is positive.

6. The control unit of claim 5, wherein the arithmetic unit is configured in the second acquisition, to additionally acquire at least one third measuring variable which represents a chemical and/or physical parameter of the gas mixture that differs from the first and second chemical and/or physical parameter, using a third sensor element, and wherein the arithmetic unit is configured in the first comparison, to additionally carry out a comparison as to whether an amount of a time derivative of the third measuring variable exceeds a third predefined threshold value.

7. The control unit of claim 6, wherein the arithmetic unit is configured in the second acquisition, to additionally acquire at least one fourth measuring variable which represents a chemical and/or physical parameter of the gas mixture that differs from the first, second and third chemical and/or physical parameter, using a fourth sensor element, and wherein the arithmetic unit is configured in the first comparison, to additionally compare whether an amount of a time derivative of the fourth measuring variable exceeds a fourth predefined threshold value.

8. The control unit of claim 5, wherein the arithmetic unit is configured in the second comparison, to determine in a positive comparison when a relative deviation of the amount between the at least one further first measuring variable and the starting measuring variable is smaller than a fifth predefined threshold value, in particular smaller than 5%.

9. A gas sensor to detect a gaseous substance and/or ethanol, in a gas mixture, comprising:
   a control unit;
   a first sensor element; and
   a second sensor element;
   wherein the control unit includes:
      a memory unit; and
      an arithmetic unit configured to perform the following:
         in a first acquisition, to acquire at least one first measuring variable which represents a first chemical and/or physical parameter of the gas mixture, in particular a concentration of ethanol, using the first sensor element, and
         in a second acquisition, to acquire at least one second measuring variable which represents a second chemical and/or physical parameter of the gas mixture that differs from the first chemical and/or physical parameter, in particular a temperature, a pressure or a humidity, using the second sensor element,
         in a first comparison, to carry out a comparison as to whether an amount of a time derivative of the first measuring variable exceeds a first predefined threshold value and whether an amount of a time derivative of the second measuring variable exceeds a second predefined threshold value,
         in a first specification, to specify a starting instant and a starting measuring variable, corresponding to the starting instant, of the first chemical and/or physical parameter when the first comparison is positive,
         in a third acquisition, to detect at least one further first measuring variable,
         in a second comparison, to compare whether the at least one further first measuring variable corresponds to the starting measuring variable,
         in a second specification, to specify an end instant when the second comparison is positive,
         in a third comparison, to compare whether the amount of a difference between the end instant and the starting instant is greater than a predefined minimum time span, and
         in a signal-generation, to generate an output signal when the third comparison is positive.

10. The gas sensor of claim 5, wherein the gas sensor is a breath gas sensor.

* * * * *